United States Patent

Wallschlaeger

Patent Number: 5,875,225
Date of Patent: Feb. 23, 1999

[54] SPIRAL SCAN COMPUTED TOMOGRAPHY APPARATUS, AND METHOD FOR IMAGE RECONSTRUCTION THEREIN

[75] Inventor: Heinrich Wallschlaeger, Erlangen, Germany

[73] Assignee: Siemens Aktiengesellschaft, Munich, Germany

[21] Appl. No.: 867,944

[22] Filed: Jun. 3, 1997

[30] Foreign Application Priority Data

Jun. 27, 1996 [DE] Germany .................. 196 25 863.4

[51] Int. Cl.$^6$ .................................................. A61B 6/03
[52] U.S. Cl. ............................................ 378/15; 378/901
[58] Field of Search ............................ 378/4, 15, 901

[56] References Cited

U.S. PATENT DOCUMENTS

| | | | |
|---|---|---|---|
| 5,345,381 | 9/1994 | Wallschlaeger | 378/15 |
| 5,473,658 | 12/1995 | Wallschlaeger | 378/15 |
| 5,530,731 | 6/1996 | Polacin et al. | 378/15 |
| 5,625,660 | 4/1997 | Tuy | 378/15 |

OTHER PUBLICATIONS

"Principles and Performance of Spiral CT," Kalender, Medical CT & Ultrasound, Current Technology and Applications, Goldman et al. Eds., pp. 379–410 (1975).

Excerpt from MATLAB© High–Performance Numeric Computation and Visualization Software, Reference Guide, pp. 82, 201, 204 and 429 (1992).

*Primary Examiner*—David P. Porta
*Assistant Examiner*—David Vernon Bruce
*Attorney, Agent, or Firm*—Hill & Simpson

[57] ABSTRACT

In a spiral scan computed tomography apparatus, and a method for reconstructing an image from spiral scan data, a measurement system composed of an x-ray source and a radiation receiver is rotated in a plane around an examination subject on a support table, while producing a feed of the support table relative to the rotation plane of the measurement system. Radiation emitted by the x-ray source, attenuated by the patient, strikes the radiation receiver, thereby producing measured signals representing spiral attenuation values. A computer is supplied with the spiral attenuation values and generates weighted spiral attenuation values therefrom using a weighting generator, by which data from a number of planar image superimpositions are employed. The number of superimpositions, the spacing of the superimpositions, and the strength of a $k^{th}$ superimposition contribution can be independently selected. An image of a volume of the patient is reconstructed from the weighted spiral attenuation values produced by the weighting generator, and the image is visually displayed.

6 Claims, 4 Drawing Sheets

SPIRAL SCAN COMPUTED TOMOGRAPHY APPARATUS, AND METHOD FOR IMAGE RECONSTRUCTION THEREIN

BACKGROUND OF THE INVENTION

1. Field of the Invention

The present invention is directed to a computed tomography apparatus and to a method for image reconstruction therein, and in particular to a computed tomography apparatus operable in a spiral scan mode and a method for image reconstruction from spiral scan attenuation values.

2. Description of the Prior Art

For image reconstruction by means of a computed tomography apparatus operating in a spiral mode, a measuring system, composed of an x-ray source and a radiation receiver, is rotated around the patient, who is lying on a support table, with relative longitudinal motion between the measuring system and the patient on the support table. An x-ray beam emanates from the x-ray source during operation of the computed tomography apparatus and attenuated by the patient, strikes the radiation receiver. A calculating unit evaluates the measured signals supplied by the radiation receiver during operation, which correspond to spiral attenuation values of the examination subject. In reconstruction of images of planar body slices of the examination subject attenuation values of a planar body slice are derived from the spiral attenuation values acquired from revolutions of the measurement system around the examination subject.

In computed tomography, registration of spiral scans i.e., obtaining spiral attenuation values of body slices of an examination subject, has become a standard technique with great significance for practical application (see, for example, Willy A. Kalender, Principles and Performance of Spiral CT, in L. W. Goldman and J. B. fowlkes, editors, MEDICAL CT and ULTRASOUND: Current Technology and Applications, pages 379–410, Advanced Medical Publishing, 1995). As noted above, the registration of spiral attenuation values usually ensues with a radiological measurement system that continuously moves around an examination subject lying on a patient support table, and the patient support table with the examination subject thereon usually moves with a constant and continuous table feed relative to the measurement system, for example in the z-direction of a Cartesian coordinate system, as shown in FIG. 1. FIG. 1 shows a computed tomography system with the aforementioned measurement system and the patient support table. Due to the relative motion of the patient support table relative to the radiological measurement system, a continuous, spiral scan motion of the radiological measurement system around the examination subject is obtained, so that the spiral attenuation values arise at the different z-positions in the radiological exposures. The z-coordinate of a data set of spiral attenuation values thereby characterizes the relative position of the measured slice represented by the spiral attenuation values of the subject. The movement of the patient support table normally ensues substantially at a right angle relative to the measurement plane, that is defined by the radiological measurement system (see FIG. 1).

For example, U.S. Pat. No. 5,473,658 discloses a computed tomography system for conducting a spiral scan wherein a computer, based on an initial image in the plane of a reference projection and an auxiliary image, recursively calculates a new image at the spacing of $d/N_{2\pi}$ from the initial image, whereby d is the slice thickness $N_{2\pi}$ is the number of projections on the circumferential angle $2\pi$. Only data from the region of a slice thickness d are utilized for each image.

Several important advantages are achieved with spiral computed tomography compared to planar computed tomography. First, a fast scan of a given volume can be accomplished, and second, the position and the spacing of the images of body slices of an examination subject to be reconstructed can be selected independently of the measurement of the spiral attenuation values, i.e. even after the measurement of the spiral attenuation values. As already mentioned, the spiral data in spiral computed tomography arise at different z-positions, but the known reconstruction algorithms for image calculation generally only work with attenuation values that are produced given a constant z-position of the measurement system. Therefore, attenuation values that correspond to a planar body slice of the examination subject must be generated with the assistance of spiral algorithms before the actual image reconstruction from the spiral attenuation values.

Spiral algorithms that were previously developed are either interpolation methods or weighting methods. The interpolation methods calculate attenuation values for a planar data set, generally from spiral attenuation values respectively in front of and behind the desired image plane, with respect to which an image of the corresponding body slice of an examination subject is to be reconstructed. The known weighting methods usually operate by resorting calculating steps from interpolation methods. Spiral algorithms are effective in terms of image quality in the reconstructed image of a planar body slice of an examination subject particularly as a result of their influence on the noise amplitude and on the slice sensitivity profile. The sensitivity profile indicates the contrast with which a subject detail, that is extremely thin in the slice thickness direction, is imaged in a reconstructed image dependent on its position along an axis parallel to the system axis (see FIG. 1, rotational axis A). Whereas, dependent on the spiral algorithm, the noise can be higher or lower in a conventional exposure, the slice sensitivity profile is usually broader than in the case of a conventional planar exposure. Given a slice gating d, FIG. 2 shows the broadening of the slice sensitivity profile $E_s$ compared to the ideal, rectangular slice sensitivity profile $E_i$, with the relative sensitivity being shown over the position of the measurement system. A x-ray beam 4 emanating from a focal spot 13 is gated onto a detector 15 with the assistance of two diaphragms 14. It is thus clear that, in addition to the slice thickness, the course of the slice sensitivity profile is also required for evaluating the image quality of a CT system. The contribution of the neighboring layer to the reconstructed image of a desired body slice of the examination subject, and the occurrence of partial-volume artifacts in the image (which shall be explained later) due to object details acquired at the edge of the slice, become lower as the edges of the slice sensitivity profiled become steeper. Known methods (see Willy A. Kalender, Principles and Performance of Spiral CT, in L. W. Goldman and J. B. fowlkes, editors, MEDICAL CT and ULTRASOUND: Current Technology and Applications, pages 379–410, Advanced Medical Publishing, 1995) essentially differ on the basis of the spacing of the interpolation partners and the type of interpolation function. In practice, however, these methods have some disadvantages, as a result of which the aforementioned advantages of spiral computer tomography do not take full effect.

When, for example a few high-contrast objects or parts thereof, for example bones, project only partially into the measured slice, a partial-volume artifact arises that causes a modification of the spiral attenuation values of the object part and its environment, and thus the object contour can also be modified. This artifact becomes more frequent as the thickness of the slice used for the measurement becomes broader (thicker). A reduction of the slice width in fact reduces the occurrence of the artifact, but increases the noise amplitude at the same time.

Further, known spiral algorithms have the inherent consequence of non-uniformly modulating the noise amplitude within a reconstructed image as well as given three-dimensional image reconstruction in the z-direction to varying degrees, which can have an extremely disturbing effect when viewing the image, and may cause the physician to make misinterpretations.

Moreover, if one wishes to evaluate parts of a subject volume with different slice thicknesses with known spiral algorithms, additional measurements respectively made with various settings of the diaphragm in front of the x-ray source are required for this purpose, i.e. with different slice gatings d (also see FIG. 2), with the result of increased radiation exposure for the examination subject. This is particularly unpleasant in the calculation of three-dimensional presentations of regions of an examination subject, since it leads to an anisotropy of the resolution.

An attempt has been made to overcome the recited disadvantages of known spiral algorithms by averaging images, but this approach requires such high image calculating times as to make it impractical, and it precludes the determination of immediate images, i.e., offering the calculated images immediately after the end of the measurement event.

SUMMARY OF THE INVENTION

An object of the present invention is to provide a spiral scan computed tomography method which avoids, or at least minimizes, the occurrence of partial-volume artifacts, noise inhomogeneities, and resolution anisotropies in reconstructed images of body slices of an examination subject, and wherein the calculating time is shortened for the reconstruction of images.

According to the invention, this object is achieved by a method for image reconstruction for a computed tomograph apparatus operating in spiral mode wherein for determining attenuation values $\hat{S}(\alpha,\beta)$ for the reconstruction of images of planar body slices of the examination subject given spiral attenuation values $S(\alpha,\beta)$ acquired from revolutions of the measurement system around the examination subject, and proceeding from an arbitrary weighting method $$\hat{S}(\alpha,\beta)=g\,(\alpha,\beta)\,S\,(\alpha+\alpha_r-0.5\alpha_G,\beta) \quad (1)$$

A weighting procedure (weighting generator)

$$\hat{S}(\alpha,\beta) = \left[\sum_{k=1}^{N_s} g_k g(\alpha-(k-1)\alpha_s,\beta)\right] S(\alpha+\alpha_r-0.5\alpha_W,\beta) \quad (2)$$

is applied, wherein $\hat{S}(\alpha,\beta)$ is the weighted spiral attenuation value, i.e., the weighted spiral attenuation value of a planar body slice;

$S(\alpha,\beta)$ is the spiral attenuation value;

$g(\alpha,\beta)$ is the spiral weight;

$\beta\in[0;\alpha_w]$ is the projection angle;

$\alpha_w=\alpha_G+(N_s-1)\alpha_s$ is the maximum projection angle;

$\alpha_G$ is the generator (procedure) dependent, maximum projection angle;

$\beta$ is the fan angle;

$\alpha_r$ is the projection angle of the reference projection whose position with respect to the motion direction of the patient support table indicates the position of the image plane of the weighted data set of spiral attenuation values $N_s$ is the number of superimpositions;

$\alpha_s=2\pi(\Delta z_s/z_u)$ is the spacing of the superimpositions;

$\Delta z_s$ is the image spacing of the images to be reconstructed;

$z_u$ is the table feed per revolution of the measurement system; and $g_k$ is strength of the $k^{th}$ superimposition contribution, with $$\left(\sum_{k=1}^{N_s} g_k = 1\right)$$

As a result of the introduction of additional degrees of freedom, a number of superimpositions $N_s$, a spacing of the superimpositions $\alpha_s$ and strengths of the $k^{th}$ superimposition contribution $g_k$, a spiral algorithm is generated that avoids or at least reduces the described disadvantages of previously known spiral algorithms. Compared to the prior art, the spiral algorithm characterized by Equation 2 provides the further advantage that, because the calculation operates on raw data (measured data), only the number of images of body slices of an examination subject are reconstructed which is required by the physician for diagnosis. This reduces the calculating time for such superimposition images compared to the number superimpositions of images that is frequently required in spiral computed tomography employing a modified planar reconstruction algorithm, so that the physician can reliably recognize details in the tomograms of an examination subject, thus reducing the calculating time by the factor $N_s$. Further, a time advantage arises because noticeably fewer images are required because of the high effective slice thicknesses of the inventive superimposition method for covering a specific subject volume, compared to spiral images produced by conventional methods with small slice thicknesses. The evaluation by the physician thus requires correspondingly less time and the documentation outlay is also reduced. When, for example, $N_s=4$, $\alpha_s=\pi$ and $g_1=g_2=g_3=g_4=0.25$ are selected for a known interpolation algorithm known as 180 LI (180° linear interpolation) (Willy A. Kalender, Principles and Performance of Spiral CT. In L. W. Goldman and J. B. Fowlkes, editors, MEDICAL CT and ULTRASOUND Current Technology and Applications, pages 379–410, which employs data for interpolation that are measured at positions lying 180° opposite one another in a measurement system formed of an x-ray source and of a radiation receiver), then the calculating time and the number of images for covering a predetermined volume are reduced in the inventive method by a factor of about four compared to the spiral individual images of small slice thickness.

One version of the inventive method provides for the selection of the following parameters:

| | |
|---|---|
| Number of superimpositions | $N_s - 2$, |
| Spacing of the superimpositions | $\alpha_s = \pi$ and |
| Strength of the $k^{th}$ superimposition contribution | $g_1 = g_2 = 0.5$ |

The image reconstruction thus ensues upon application of the method $$\hat{S}(\alpha,B)=0.5[g\,(\alpha,B)+g(\alpha-\pi,\beta)]\cdot S\,(\alpha+\alpha_r-0.5\pi-0.5\alpha_G,\beta) \quad (3)$$

with $\alpha \in [0; \alpha_G + \pi]$.

In this superimposition method, the spatial modulation of the noise amplitude, i.e. the noise inhomogeneity, is significantly reduced in reconstructed images of a body slice of an examination subject compared to the original method according to Equation 1.

A further version of the invention provides for the selection of the following parameters:

| | |
|---|---|
| Number of superimpositions | $N_s = 4$, |
| Spacing of the superimpositions | $\alpha_s = \pi \bar{d}_{eff} z_u$, and |
| Strength of the $k^{th}$ superimposition contribution | $g_1 = g_2 = g_3 = g_4 = 0.25$ |

The image reconstruction then ensues by employment of the method $$\hat{S}(\alpha, \beta) = 0.25 \sum_{k=1}^{4} g(\alpha - (k-1)\alpha_s, \beta) S(\alpha + \alpha_r - 1.5\alpha_s - 0.5\alpha_G, \beta) \quad (4)$$

wherein $\alpha \in [0; \alpha_W = \alpha_G + 3\alpha_S]$ is the projection angle $\bar{d}_{eff}$ is the effective slice thickness of an arbitrary weighting method, as the initial method; and $z_u$ is the table feed per revolution of the x-ray beam.

In this case, partial-volume artifacts are reduced in reconstructed images of body slices of an examination subject, with $\bar{d}_{eff}$ being the effective slice thickness (Full Width at Half Maximum), i.e. the width of the slice sensitivity profile at half the maximum value of, for example, the initial method of Equation 1, and with $z_u$ being the table feed of the patient support table per revolution of the measurement system around the examination subject. This superimposition method achieves the low artifact amplitude as is achieved by a measurement with a small slice gating d, together with the low noise amplitude as is achieved by a method with slice gating that is twice as big, thereby representing a significant improvement over conventional methods. Moreover, this method also reduces the inhomogeneity of the noise amplitude.

A further version of the inventive method includes the additional method step that an accumulation of weighted spiral attenuation values $\hat{S}(\alpha, \beta)$ ensues according to $$\tilde{S}(\alpha, \beta) = \sum_{k=1}^{N(\alpha)} \hat{S}(\alpha + (k-1)2\pi, \beta) \quad (5)$$

with $\alpha \in [0; 2\pi]$ and $N(\alpha) = \text{ceil}[(\alpha_W - \alpha)/(2\pi)]$, whereby ceil (x) is the smallest integer number greater than x.

The possibility thus exists of reducing the time for the image calculation according to the inventive method to the image calculating time of a planar 360° image of a body slice of an examination subject, whereby the projection angle $\alpha$ only runs from 0–$2\pi$. The attenuation values $\tilde{S}(\alpha, \beta)$ are then supplied to the subsequent mathematical operations of convolution and back-projection during the course of the image reconstruction.

A computed tomography apparatus for the implementation of the inventive method works in spiral mode and has a calculating unit that operates according to the inventive method in the image reconstruction, whereby the parameters of a number of superimpositions $N_S$, a spacing of the superimpositions $\alpha_s$ and a strength of the $k^{th}$ superimposition contribution $g_k$, can be set independently of one another.

By variation of the parameters, a number of superimpositions $N_s$, a spacing of the superimpositions $\alpha_s$, and a strength of the $k^{th}$ superimposition contribution $g_k$, for example, the noise amplitude can be set independently of the measured spiral attenuation values in the images of body slices of an examination subject to be reconstructed. Further, the effective slice thickness $d_{eff}$ belonging to a slice gating d (also see FIG. 2) can be set independently of the measured spiral attenuation values in the images to be reconstructed. This is of particular significance in conjunction with three-dimensional reconstruction of tomograms of an examination subject and in the conversion onto inclined planes. Normally, it allows the image resolution in the axial direction (z-direction) to be matched to the image resolution in the image plane, i.e. in the plane of the body slice. To this end, the superimposition method suitably parameterized for a given reconstruction core must merely be applied, with a three-dimensional isotropy of the image resolution being thereby achieved.

DESCRIPTION OF THE PREFERRED EMBODIMENTS

Figure 1:
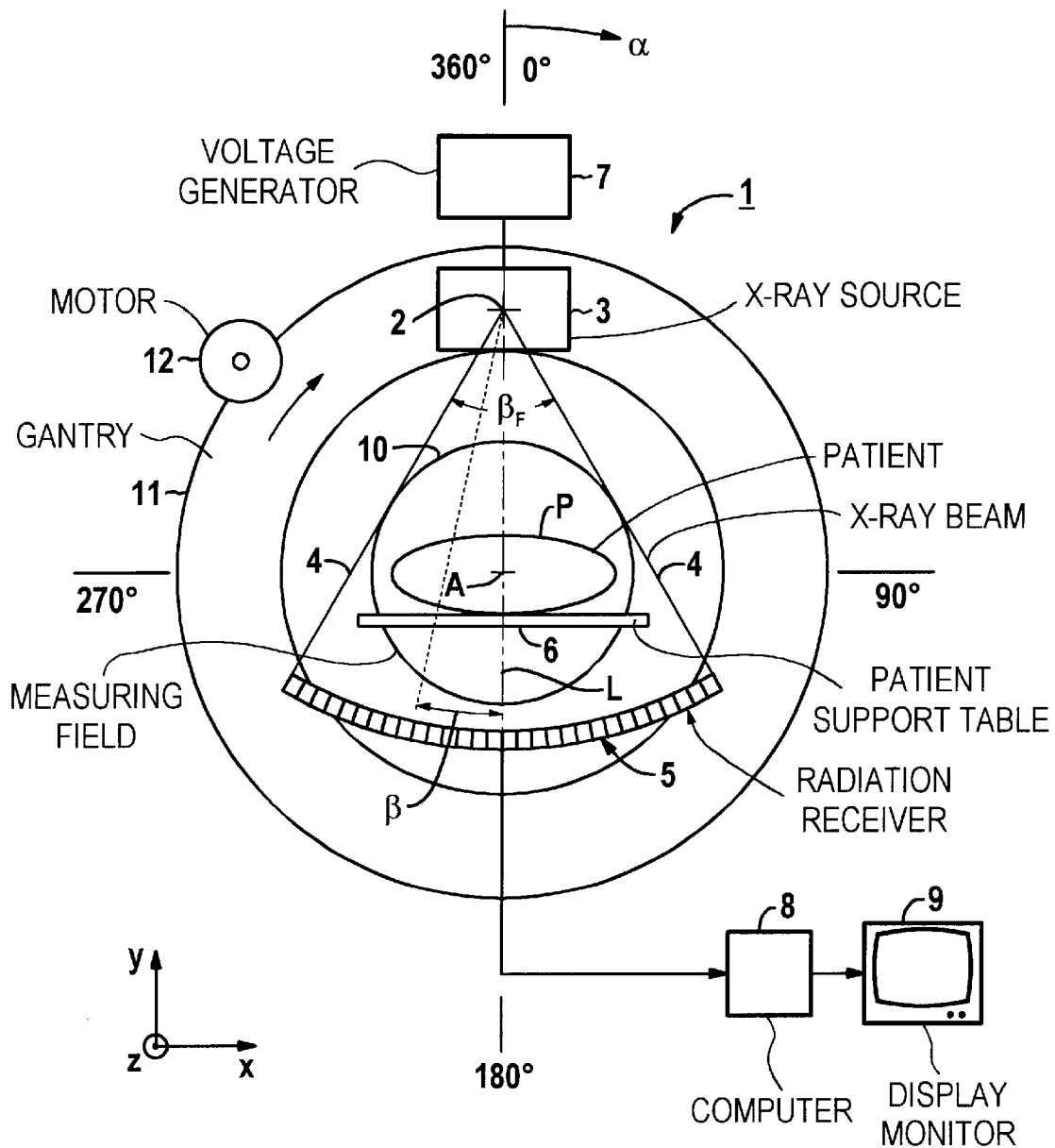
FIG. 1 is a schematic illustration of a computed tomography apparatus for the implementation of the inventive superimposition method.

FIG. 1 shows a computed tomography apparatus 1 for the implementation of the inventive method for generating attenuation values $\hat{S}(\alpha, \beta)$ which correspond to a planar body slice (in the x-y plane of the Cartesian coordinate system entered in FIG. 1) of a patient P to be examined from measured spiral attenuation values $S(\alpha, \beta)$. The computed tomography apparatus 1 has a measurement system composed of an x-ray source 3 that emits a fan-shaped x-ray beam 4, and a radiation receiver 5 that is composed of a row of individual detectors. The focus of the x-ray source 3 from which the x-ray beam 4 emanates is referenced 2. The patient P to be examined lies on a patient support table 6.

For conducting a radiological examination of the patient P, the measurement system rotates around a measuring field 10 in which the patient P lies. To this end, a motor 12 drives the rotating gantry 11. The rotational axis, which proceeds substantially in the z-direction of the Cartesian coordinate system entered in FIG. 1, resides substantially at a right-angle relative to the fan-shaped x-ray beam 4, and is referenced A. During a radiological examination, the patient support table 6 with the patient P thereon usually moves continuously with constant table feed $z_u$ in the z-direction of the coordinate system entered in FIG. 1. Due to the relative motion of the patient support table 6 relative to the radiological measurement system which essentially rotates in the x-y plane of the Cartesian coordinate system entered in FIG. 1, one obtains a continuous, spiral scan motion of the radiological measurement system around the patient P. The x-ray source 3 is fed by a voltage generator 7 and is operated with continuous radiation emission during scan motion. In this way, projections (attenuation profiles) of slices of the patient P are registered, and the appertaining data sets of the measured data (spiral attenuation values) are supplied from the radiation receiver 5 to a calculating unit 8 that intermediately stores and evaluates the data sets. From the spiral attenuation values $S(\alpha,\beta)$ measured in a fast volume scan of the patient P with the computer tomograph 1 and intermediately stored in the calculating unit 8, attenuation values $\hat{S}(\alpha,\beta)$ of planar body slices of the patient P are calculated in the calculating unit 8 according to the inventive method, and are supplied in a known way for convolution and for back-projection within the framework of the image reconstruction of body slices of a patient P. Finally, the attenuation coefficients of predetermined picture elements are calculated in the computer 8 from the generated data sets and are visually reproduced on a monitor 9. Accordingly, an image of the transirradiated slice of the patient P appears on the monitor 9.

For calculating attenuation values $\hat{S}(\alpha,\beta)$ of a planar body slice as spiral attenuation values $S(\alpha,\beta)$, an arbitrary weighting version according to the Equation 1 is applied $$\hat{S}(\alpha,\beta) = g(\alpha,\beta) S(\alpha+\alpha_r-0.5\alpha_G,\beta) \quad (1)$$

Figure 3:
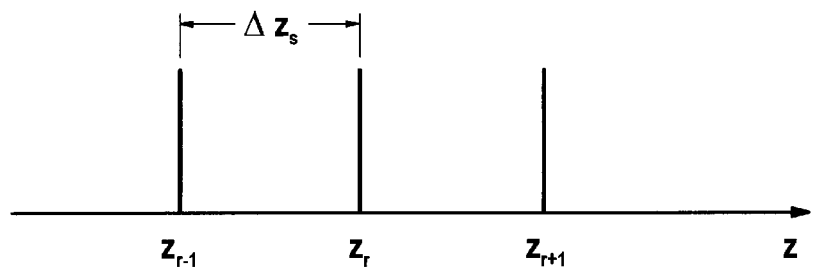
FIG. 3 shows the spacing $\Delta z_s$ of reconstructed images of body slices of a patient in the axial direction (z-direction).

$S(\alpha,\beta)$ is the spiral attenuation value in the channel having the fan angle $\beta$ of the projection with the projection angle $\alpha$. The fan angle $\beta$ is indicated with reference to a line L lying in the middle of the fan-shaped x-ray beam 4, which need not necessarily proceed through a detector element of the radiation receiver 5. The term $g(\alpha,\beta)$ is the spiral weighting and $\hat{S}(\alpha,\beta)$ is the result of the weighting. The projection angle $\alpha$ thereby proceeds over an angular interval from 0 up to a method-dependent, maximum projection angle $\alpha_G$. The parameter $\alpha_r$ indicates the projection angle of the reference projection whose z-position (see FIG. 3, $z_R$ defines the position of the image plane of the weighted data set of spiral attenuation values $\hat{S}(\alpha,\beta)$. The aforementioned method 180LI with $$g(\alpha,\beta) = \frac{\alpha + 2\beta \pm \pi - \pi - \beta_F}{2\beta \pm \pi} + \left| \frac{\alpha + 2\beta \pm \pi - \pi - \beta_F}{2\beta \pm \pi} \right| \quad (6)$$

is recited an example of a spiral weighting $g(\alpha,\beta)$ The plus sign in Equation 6 is valid for $\alpha<\pi+\beta_F$, the minus sign is valid for $\alpha y \geq \pi+\beta_F$ where $\beta_F$ is the full fan angle and $\alpha_G=2(\pi+\beta_F)$ is the maximum projection angle for the method 180 LI.

Whereas only one spiral weighting is taken into consideration in known methods, a superimposition of a number of spiral weightings ensues in the inventive method. One therefore uses the additional parameters of the number of superimpositions $N_s$, the spacing of the superimpositions $\alpha_s$ and the strength of the $k^{th}$ superimposition contribution $g_k$. Proceeding from an arbitrary weighting method according to Equation 1, one thus obtains $$\hat{S}(\alpha,\beta) = \left[ \sum_{k=1}^{N_s} g_k g(\alpha - (k-1)\alpha_s, \beta) \right] S(\alpha + \alpha_r - 0.5\alpha_w, \beta) \quad (2)$$

for the most general case of the inventive superimposition method.

Figure 4:
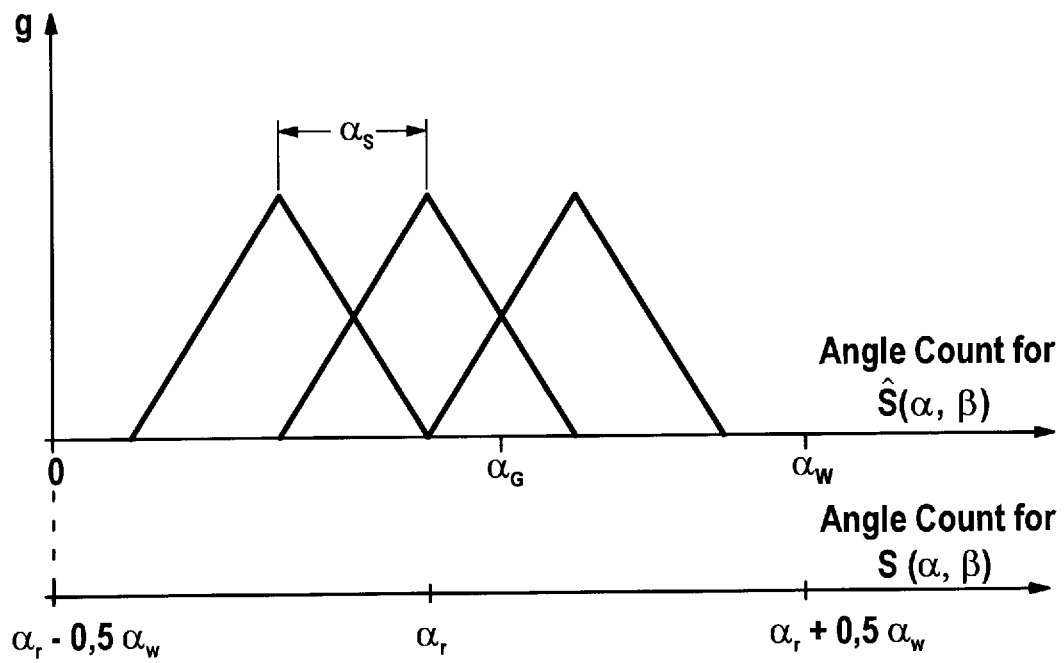
FIG. 4 shows an example of the inventive superimposition method with superimpositions of $N_S = 3$ spiral weightings.

FIG. 4 shows an example of the inventive superimposition method according to Equation 2 with $N_s=3$ superimposed spiral weightings $g(\alpha,\beta)$. The parameter $\alpha_r$, as in the case of the arbitrary weighting method, is the projection angle of the reference projection whose z-position (see FIG. 3, $z_r$) indicates the position of the image plane of the weighted data set of spiral attenuation values $\hat{S}(\alpha,\beta)$. The projection angle $\alpha$ according to the inventive method proceeds from zero through $\alpha_w=\alpha_G+2\alpha_s$ in the present case, with projections of body slices of the patient P being continuously registered in this angular interval. The spacing of the superimpositions $\alpha_s$ is thereby freely selectable dependent on the calculation case, and is calculated according to $2\pi \Delta z_s/z_u$, whereby $\Delta z_s$ is the image spacing of the images to be reconstructed and $z_u$ is the table feed of the patient support table per revolution of the measurement system around the rotational axis A, or the movement of the patient P in the z-direction of the coordinate system entered in FIG. 1. The spiral weightings $g(\alpha,\beta)$, moreover, are assigned different relative weightings with the superimposition contributions $g_k$, whereby the sum over the superimposition contributions $g_k$ is equal to 1. For calculating attenuation values $\hat{S}(\alpha,\beta)$ of a planar body slice of the patient P at the z-position $Z_r$, all spiral attenuation values $s(\alpha,\beta)$ measured in the two angular intervals $[\alpha_r-0.5\alpha_w;\alpha_R]$ and $[\alpha_r; \alpha_r+0.5\alpha_x]$ lying symmetrically around the projection angle of the reference projection $\alpha_r$ are utilized, with each spiral attenuation value $S(\alpha,\beta)$ being weighted in the present case with three superimposed spiral weightings $g(\alpha,\beta)$ that have the spacing $\alpha_s$ from one another. The superimposition contributions $g_1$ through $g_3$ of the three superimposed spiral weightings $g(\alpha,\beta)$ in the present case each have the value ⅓, so that $$\hat{S}(\alpha,\beta) = \frac{1}{3} \left[ \sum_{k=1}^{3} g(\alpha - (k-1) \cdot \alpha_s, \beta) \right] S(\alpha + \alpha_r - 0.5\alpha_w, \beta) \quad (7)$$

is valid overall.

The superimposition contributions $g_1$ through $g_3$, moreover, need not all have the same value, but can assume values other than ⅓, but as mentioned, the sum of the superimposition contributions must be equal to 1.

Proceeding from the general, inventive superimposition method according to Equation 2, there are various embodiments that, on the basis of different selection of the parameters of the number of superimpositions, the spacing of the superimpositions and the strength of the $k^{th}$ superimposition contribution, exhibit specific properties and lead to other image results.

Figure 5:
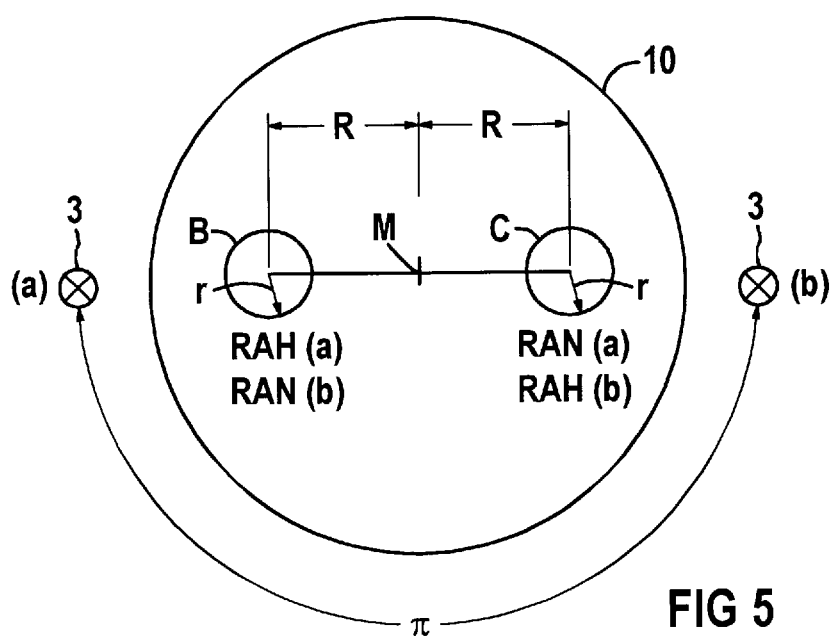
FIG. 5 is a schematic illustration showing the reduction of the noise inhomogeneity in an image to be reconstructed according to a version of the inventive method.

When, for example, the number of superimpositions is selected $N_s=2$, the spacing of the superimpositions is selected $\alpha_s=\pi$ and the strength of the $k^{th}$ superimposition contribution is selected $g_1=g_2=0.5$, one obtains the method $$\hat{S}(\alpha,B)=0.5[g(\alpha,B)+g(\alpha-\pi,\beta)] \cdot S(\alpha+\alpha_r-0.5\pi-0.5\alpha_G,\beta) \quad (3)$$

wherein the spatial modulation of the noise amplitude is significantly reduced compared to the initial method according to Equation 1. As schematically illustrated in FIG. 5, it is assumed that the noise amplitude (RA) in the registration of spiral attenuation values is high (RAH (a)) in the position $\alpha$ of the radiation source 3 in a circular region B with the radius r that has the spacing R from the mid-point of the measurement field 10 under consideration, The example of FIG. 5 also assumes the noise amplitude is low (RAN (a))in a circular region C that likewise has the radius R and that likewise has the spacing R from the mid-point of the measurement field 10 under consideration, The mid-points of the circular regions B and C lie on a common connecting line that proceeds through the mid-point M of the measurement field 10. This case is exactly reversed (B=RAN(b), C=RAH(b)) given a revolution of the radiation source 3 around $\alpha_s=\pi$, so that the radiation source 3 is situated at position b, When, consequently, the spiral attenuation values $S(\alpha,\beta)$ measured in the positions A and B of the radiation source 3 are superimposed in the determination of the attenuation values $\hat{S}(\alpha,\beta)$ of a planar body slice of a patient P according to the inventive method according to Equation 3, the spatial modulation of the noise amplitude is reduced, so that the noise inhomogeneity in the reconstructed image is reduced.

Further, on the basis of a corresponding selection of the parameters of the number of superimpositions $N_S$, the spacing of the superimposition $\alpha_S$ and the strength of the $k^{th}$ superimposition contribution $g_k$ according to the inventive superimposition method, the noise amplitude in the reconstructed image can be set independently of the measurement of the spiral attenuation values $S(\alpha,\beta)$. When, for example, $N_S=2$, $\alpha_s=2\pi\cdot\xi(0\leq\xi\leq 0.5)$ and $g_1=g_2=0.5$ are selected, then one obtains the method $$\hat{S}(\alpha,\beta)=0.5\ [g(\alpha,\beta)+g(\alpha-2\pi\xi,\ \beta)]S(\alpha+\alpha_r-\xi\pi-0.5\alpha_G,\beta), \quad (8)$$

whereby the projection angle $\alpha$ runs from 0 through $\alpha_W=\alpha_G+2\pi\cdot\xi$. The noise amplitude can be varied with the parameter $\xi$. When, for example, a planar reference image of a body slice of the patient P, i.e. an image of a body slice that was determined from attenuation values measured given a constant z-position of the measurement system 3, 5, has the noise amplitude $\rho_0$, then the superimposition method according to Equation 8—applying the example 180LI—leads to a noise amplitude $$\sigma = \sqrt{4\xi^3 - 4\xi^3 + \frac{4}{3}}\ \sigma_0. \quad (9)$$

When the parameter $\xi$ is selected according to Equation 10 as $$\xi_T = \frac{1}{3} + \frac{2}{3}\ \cos\left\{\ \frac{1}{3}\ \arccos\left(-\frac{1}{8}\right) + \frac{3}{4}\ \pi\ \right\} = 0.3612 \quad (10)$$

the noise amplitude in the reconstructed image of the body slice of the patient P, which arises as a result of the employment of the superimposition method according Equation 8 is of exactly the same size as in the reference image. The reference image is an image for whose measurement and calculation—given the same subject (patient P)—identical values were utilized for the slice gating d, for filtering, tube voltage, tube current, zoom, image center and reconstruction core as in the reconstructed image upon employment of Equation 8.

Figure 2:
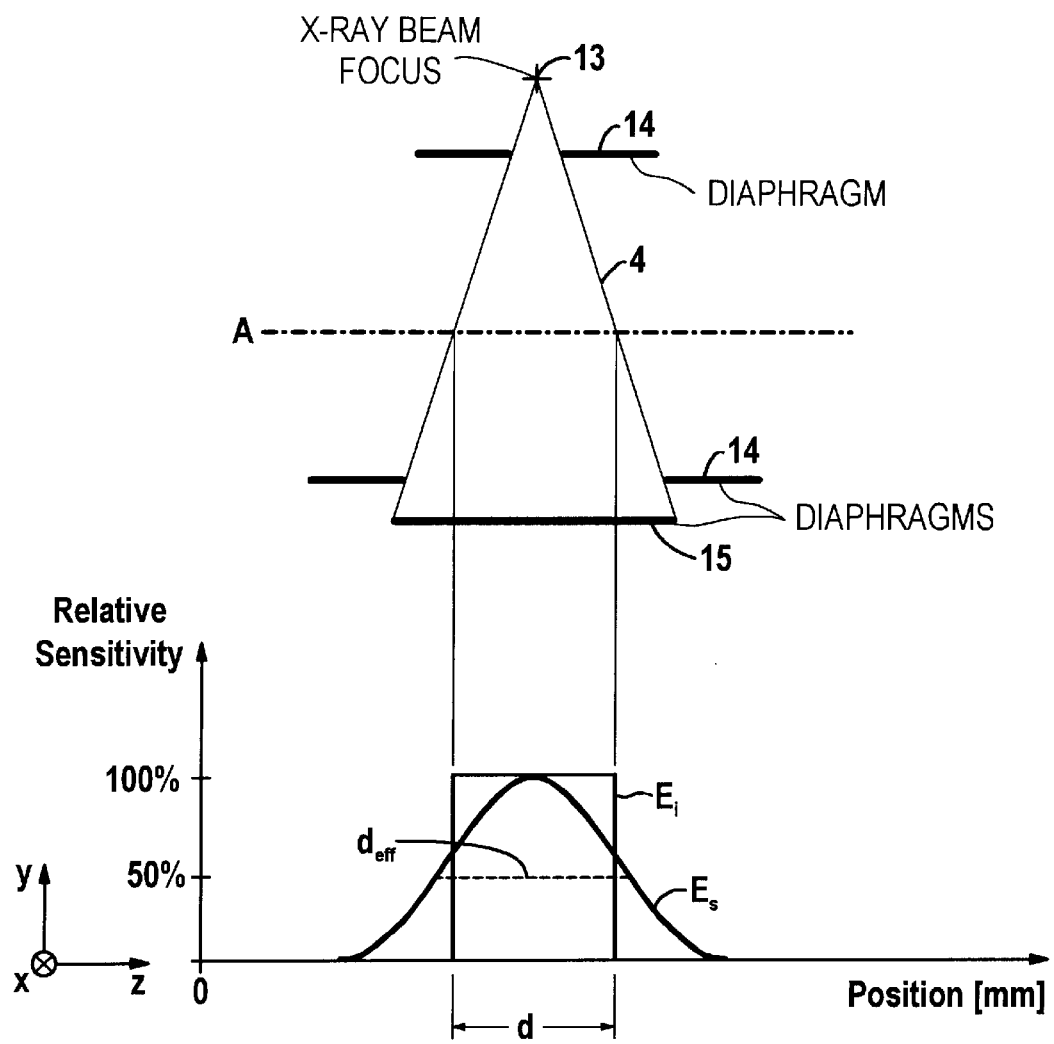
FIG. 2 is a schematic illustration showing the generation of an optimally rectangular slice sensitivity profile by suitable, detector-proximate gating of the x-ray beam and the broadening of the slice sensitivity profile in the spiral CT.

Further, with an appropriate selection of the parameters of numbers of superimpositions $N_S$, spacing of the superimpositions $\alpha_S$ and strength $k^{th}$ superimposition contribution $g_k$, the effective layer thickness $d_{eff}$ belonging to a slice gating d can be set independently of the measured spiral attenuation values $S(\alpha,\beta)$ in the images to be reconstructed. When, as in the case described above, $N_S=2$, $\alpha_S=2\pi\cdot\xi(0\leq\xi\leq 0.5)$ and $g_1=g_2=0.5$ are again selected, then, in the case of the example 180LI, this superimposition method according to Equation 8 given a table feed $z_u=d$ corresponding to the slice gating d (see FIG. 2) leads to an effective slice thickness $$d_{eff} = \frac{1}{1-\xi}\ \left\{\ \frac{1}{4}\ (1+\xi)^2 - \frac{3}{2}\ \xi + \frac{3}{4}\ \right\}\ d \quad (11)$$

In this case, the effective slice thickness $d_{eff}$ can be varied by variation of the parameter $\xi$. As mentioned, this is of particular interest in conjunction with the reconstruction of three-dimensional images and in the conversion onto inclined planes since it is thereby possible to match the resolution of images in the axial direction (z-direction) to the resolution of the images in the image plane (x-y-plane).

If partial-volume artifacts occur in the reconstructed images from spiral attenuation values, then a method with $N_S=4$, $\alpha_s=\pi\cdot\overline{d}_{eff}/z_u$ and $g_1=g_2=g_3=g_4=0.25$ proves especially beneficial, $$\hat{S}(\alpha,\beta) = 0.25\ \sum_{k=1}^{4}\ g(\alpha - (k-1)\alpha_s,\ \beta)S(\alpha + \alpha_r - 1.5\alpha_s - 0.5\alpha_G,\ \beta) \quad (4)$$

whereby the projection angle $\alpha$ runs from 0 to $\alpha_w=\alpha_G+y3\alpha_S$. The value $\overline{d}_{eff}$ is the effective layer thickness of the initial method according to Equation 1 and $z_u$ is the table feed per revolution of the measurement system around the rotational axis A, or around the patient P. As already mentioned, this method achieves a low artifact amplitude of a measurement with a small slice gating d together with the low noise amplitude of a method with slice gating that is twice as big. Moreover, the inhomogeneity of the noise amplitude is also reduced. The application of the example 180LI to this superimposition method leads, compared to the reference image having the noise amplitude $\sigma_0$, to a noise amplitude of $$\sigma = \sqrt{\frac{11}{24}}\ \sigma_0\ \text{for}\ p=1, \quad (12)$$

whereby p (pitch) is the dimension-free table feed.

With a table feed $z_u=p\cdot d$, the effective slice thickness in this example amounts to approximately $$d_{eff} = 2(p + 1 - \sqrt{2p-1})\ d. \quad (13)$$

Figure 6:
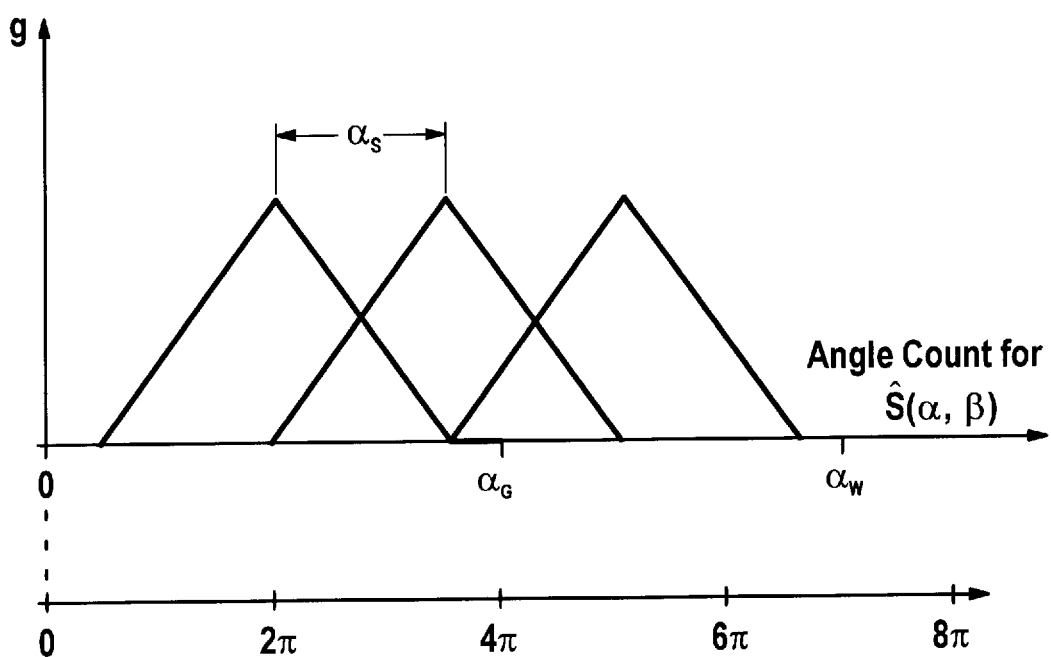
FIG. 6 shows an example for reduction of the calculating time given accumulation of weighted spiral attenuation values.

Based on the inventive method, however, the time for the image calculation can be reduced to the image calculating time of a normal 360° image of a body slice of a patient P when the weighted attenuation values are accumulated according to Equation 5.

$$\tilde{S}(\alpha,\beta) = \sum_{k=1}^{N(\alpha)} \hat{S}(\alpha + (k-1)2\pi,\ \beta) \quad (5)$$

with $N(\alpha)=\text{ceil}[(\alpha_w-\alpha)/(2\pi)]$ (ceil(x) is the smallest integer number greater than x). The projection angle $\alpha$ thereby runs only from 0 through $2\pi$. It is then the attenuation values $\tilde{S}(\alpha,\beta)$ that are supplied to the further mathematical operations of convolution and of back-projection within the framework of the image reconstruction. FIG. 6 illustrates an example for the reduction of the calculating time given accumulation of weighted spiral attenuation values with $N_S=3$. Because of $\alpha_W=7\pi$, $N(\alpha)=4$ is obvious for $0\leq\alpha\leq\pi$ and $N(\alpha)=3$ for $\pi\leq\alpha\leq 2\pi$. In the present case, thus, four or three attenuation values that were determined from spiral attenuation values are summed to form a new attenuation value $\tilde{S}(\alpha,\beta)$ that are subsequently supplied to the convolution and the back-projection, so that the image calculating time is reduced to the image calculating time of a normal 360° image of a body slice of a patient P.

It is thus achieved, on the basis of the inventive superimposition method, that the radiation exposition and the dwell time of patients can be reduced for various applications in spiral computed tomography, which are not possible with the known spiral algorithms. Given diagnostic questions for which slice sensitivity profiles of different slice widths are necessary to clarify (for example, soft tissue diagnosis and bone diagnosis in the same volume), there is thus a possibility of making the bone diagnosis with images of the initial method according to Equation 1. The soft tissue diagnosis can then be carried out using images that were calculated from the same data set with the method $N_s=4$, $\alpha_s = \pi \cdot d_{eff}/z_u$ and $g_1$ through $g_4=0.25$. The patient profits by not being exposed to the radiation of a second measurement with a greater slice thickness, and by not having to remain on the support for the duration of a second measurement.

Further, a time advantage arises when slice sensitivity profiles of different widths are required in adjoining volume parts. The exposure can then be implemented through the entire volume with a single (thin) slice, with different effective slice thicknesses which are respectively suitable for the different volume parts being selected in the image calculation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for image reconstruction in a spiral mode computed tomography apparatus comprising the steps of:

(a) placing a patient on a patient support table;

(b) conducting a spiral scan of a volume of said patient by rotating a measurement system, composed of an x-ray source and a radiation receiver, in a plane around the patient support table, while feeding said patient support table in a feed direction relative to said plane, and while emitting an x-ray beam from said x-ray source that is attenuated by said patient and strikes the radiation receiver, thereby producing measured signals from said radiation receiver comprising spiral attenuation values $S(\alpha,\beta)$;

(c) evaluating said measured signals in a computer for determining weighted spiral attenuation values $\hat{S}(\alpha,\beta)$ for reconstructing respective images of planar body slices of the patient from said spiral attenuation values $S(\alpha,\beta)$ employing a weighting generator $$\hat{S}(\alpha,\beta) = \left[ \sum_{k=1}^{N_s} g_k g(\alpha - (k-1)\alpha_s, \beta) \right] S(\alpha + \alpha_r - 0.5\alpha_W, \beta)$$

wherein $\hat{S}(\alpha,\beta)$ is a weighted spiral attenuation value of a planar body slice of said patient;

$S(\alpha,\beta)$ is a spiral attenuation value, $g(\alpha,\beta)$ is a spiral weight, $\alpha \xi [0; \alpha_W]$ is a projection angle, $\alpha_W = \alpha_G + (N_s - 1)\alpha_s$ is a maximum projection angle, $\alpha_G$ is a generator dependent, maximum projection angle, $\beta$ is a fan angle, $\alpha_r$ is a projection angle of a reference projection having a position with respect to the feed direction of the patient support table indicating a position of an image plane of a weighted data set of said spiral attenuation values, $N_s$ is a plurality of superimpositions, $\alpha_s = 2\pi(\Delta z_s/z_u)$ is spacing of said superimpositions, $\Delta z_s$ is an image spacing of the images to be reconstructed;

$z_u$ is a table feed of said patient support table per revolution of the measurement system, and $g_k$ is a strength of a $k^{th}$ superimposition contribution, with $$\left( \sum_{k=1}^{N_s} g_k = 1 \right)$$

(d) reconstructing and displaying said images.

2. A method as claimed in claim 1, where in step (c) is further defined by setting the plurality of superimpositions $N_s=2$, the spacing of the superimpositions $\alpha_s = \pi$, and the strength of the $k^{th}$ superimposition contribution $g_1 = g_2 = 0.5$.

3. A method as claimed in claim 1, wherein step (c) is further defined by setting the plurality of superimpositions $N_s=4$, the spacing of the superimpositions $\alpha_s = \pi \, \bar{d}_{eff}/z_u$, and the strength of the $k^{th}$ superimposition contribution $g_1 = g_2 = g_3 = g_4 = 0.25$, wherein $d_{eff}$ is an effective slice thickness of an arbitrary weighting generator employed as an initial weighting generator.

4. A method as claimed in claim 1 comprising the additional step of accumulating said weighted spiral attenuation values $\hat{S}(\alpha,\beta)$ according to $$\tilde{S}(\alpha, \beta) = \sum_{k=1}^{N(\alpha)} \hat{S}(\alpha + (k-1)2\pi, \beta) \tag{5}$$

wherein $\alpha \xi [0; 2\pi]$, and $N(\alpha) = \text{ceil} [(\alpha_w - \alpha)/(2\pi)]$, wherein ceil (x) is a smallest integer number greater than x.

5. A spiral mode computed tomography apparatus comprising:

(a) a patient support table for accommodating a patient to be examined;

(b) means for conducting a spiral scan of a volume of said patient by rotating a measurement system, composed of an x-ray source and a radiation receiver, in a plane around the patient support table, while feeding said patient support table in a feed direction relative to said plane, and while emitting an x-ray beam from said x-ray source that is attenuated by said patient and strikes the radiation receiver, thereby producing measured signals from said radiation receiver comprising spiral attenuation values $S(\alpha,\beta)$;

(c) computer means for evaluating said measured signals for determining weighted spiral attenuation values $\hat{S}(\alpha,\beta)$ for reconstructing respective images of planar body slices of the patient from said spiral attenuation values $S(\alpha,\beta)$ employing a weighting generator $$\hat{S}(\alpha,\beta) = \left[ \sum_{k=1}^{N_s} g_k g(\alpha - (k-1)\alpha_s, \beta) \right] S(\alpha + \alpha_r - 0.5\alpha_W, \beta)$$

wherein $\hat{}(\alpha,\beta)$ is a weighted spiral attenuation value of a planar body slice of said patient;

$S(\alpha,\beta)$ is a spiral attenuation value, $g(\alpha,\beta)$ is a spiral weight, $\alpha \xi [0; \alpha_w]$ is a projection angle, $\alpha_w = \alpha_G + (N_s - 1)\alpha_s$ is a maximum projection angle, $\alpha_G$ is a generator dependent, maximum projection angle, $\beta$ is a fan angle, $\alpha_5$ is a projection angle of a reference projection having a position with respect to the feed direction of the patient support table indicating a position of an image plane of a weighted data set of said spiral attenuation values, $N_s$ is a plurality of superimpositions, $\alpha_s = 2\pi(\Delta z_s/z_u)$ is spacing of said superimpositions, $\Delta z_s$ is an image spacing of the images to be reconstructed;

$z_u$ is a table feed of said patient support table per revolution of the measurement system, and $g_k$ is a strength of a $k^{th}$ superimposition contribution, with $$\left( \sum_{k=1}^{N_s} g_k = 1 \right)$$

(d) reconstructing and displaying said images.

6. A spiral mode computed tomography apparatus as claimed in claim 5 further comprising means for independently selecting each of said plurality of superimpositions $N_s$, said spacing of said superimpositions $\alpha_s$, and said strength of said $k^{th}$ superimposition contribution $g_k$.

* * * * *